(12) United States Patent
Dmuschewsky

(10) Patent No.: US 12,097,127 B2
(45) Date of Patent: Sep. 24, 2024

(54) IMPLANTATION TOOL FOR AN INTERPHALANGEAL IMPLANT

(71) Applicant: WALDEMAR LINK GMBH & CO. KG, Hamburg (DE)

(72) Inventor: Klaus Dmuschewsky, Hamburg (DE)

(73) Assignee: WALDEMAR LINK GMBH &CO. KG, Hamburg (DE)

( * ) Notice: Subject to any disclaimer, the term of this patent is extended or adjusted under 35 U.S.C. 154(b) by 0 days.

(21) Appl. No.: 18/250,766

(22) PCT Filed: Oct. 7, 2021

(86) PCT No.: PCT/EP2021/077686
§ 371 (c)(1),
(2) Date: Apr. 27, 2023

(87) PCT Pub. No.: WO2022/089904
PCT Pub. Date: May 5, 2022

(65) Prior Publication Data
US 2023/0390079 A1  Dec. 7, 2023

(30) Foreign Application Priority Data

Oct. 30, 2020 (EP) .................................... 20204941

(51) Int. Cl.
*A61F 2/46* (2006.01)
*A61F 2/42* (2006.01)
(52) U.S. Cl.
CPC .... *A61F 2/4606* (2013.01); *A61F 2002/4243* (2013.01); *A61F 2002/4622* (2013.01); *A61F 2002/4627* (2013.01)

(58) Field of Classification Search
CPC .................. A61F 2/4606; A61F 2/4603; A61F 2002/4243; A61F 2002/4622; A61F 2002/4627; A61B 50/30; A61B 50/33
See application file for complete search history.

(56) References Cited

U.S. PATENT DOCUMENTS 3,869,729 A 3/1975 Attenborough
5,443,516 A 8/1995 Albrektsson et al.
(Continued)

FOREIGN PATENT DOCUMENTS

CN 101325927 A 12/2008
CN 204562343 U 8/2015
(Continued)

OTHER PUBLICATIONS

International Search Report and Written Opinion mailed Jan. 28, 2022, in connection with International Patent Application No. PCT/EP2021/077686, 13 pgs.
(Continued)

*Primary Examiner* — Tracy L Kamikawa
(74) *Attorney, Agent, or Firm* — Chiesa Shahinian & Giantomasi PC

(57) ABSTRACT

The disclosure provides a tool for implanting an interphalangeal implant, an implant retainer for an interphalangeal implant, and a method for preparing an implantation tool for an implantation of an interphalangeal implant. The tool for implanting an interphalangeal implant comprises a limb support for supporting a limb, a driving rod, wherein the driving rod is movable for moving an interphalangeal implant towards the limb support, and an actuation mechanism for actuating the implant driver.

14 Claims, 3 Drawing Sheets

(56) References Cited

U.S. PATENT DOCUMENTS

| | | | |
|---|---|---|---|
| 5,667,510 A | 9/1997 | Combs | |
| 5,702,471 A | 12/1997 | Grundei et al. | |
| 6,656,178 B1* | 12/2003 | Veldhuizen | A61F 2/4455 606/279 |
| 7,625,379 B2* | 12/2009 | Puno | A61F 2/4611 606/86 A |
| 9,474,561 B2 | 10/2016 | Shemwell et al. | |
| 9,622,783 B2 | 4/2017 | Reiley et al. | |
| 9,675,392 B2 | 6/2017 | Shemwell et al. | |
| 10,357,260 B2* | 7/2019 | Triplett | A61B 17/8866 |
| 11,266,450 B2 | 3/2022 | Link et al. | |
| 2004/0167625 A1 | 8/2004 | Beyar et al. | |
| 2004/0260289 A1 | 12/2004 | Padget et al. | |
| 2007/0156241 A1 | 7/2007 | Reiley et al. | |
| 2007/0282443 A1 | 12/2007 | Globerman et al. | |
| 2010/0125301 A1 | 5/2010 | Kinmon et al. | |
| 2011/0118796 A1 | 5/2011 | Reiley et al. | |
| 2013/0066435 A1 | 3/2013 | Averous et al. | |
| 2013/0131822 A1 | 5/2013 | Lewis et al. | |
| 2015/0073413 A1 | 3/2015 | Palmer et al. | |
| 2015/0223856 A1 | 8/2015 | Tyber et al. | |
| 2016/0367300 A1 | 12/2016 | Caldarella et al. | |
| 2017/0007416 A1 | 1/2017 | Sander et al. | |
| 2017/0181770 A1 | 6/2017 | Reiley et al. | |
| 2017/0348032 A1* | 12/2017 | Barry | A61B 17/7291 |
| 2020/0179019 A1 | 6/2020 | Link et al. | |

FOREIGN PATENT DOCUMENTS

| | | |
|---|---|---|
| CN | 205339255 U | 6/2016 |
| CN | 106344218 A | 1/2017 |
| DE | 69002159 T2 | 10/1993 |
| DE | 29813030 U1 | 10/1998 |
| DE | 10354601 B3 | 6/2005 |
| DE | 202009008872 U1 | 9/2009 |
| DE | 102013210638 B4 | 3/2018 |
| EP | 1096906 A1 | 5/2001 |
| EP | 2158864 A2 | 3/2010 |
| EP | 3928747 A1 | 12/2021 |
| WO | 2011116078 A1 | 9/2011 |
| WO | 2014/195446 A1 | 12/2014 |
| WO | 2015/147846 A1 | 10/2015 |
| WO | 2018/188861 A1 | 10/2018 |
| WO | 2020/076376 A1 | 4/2020 |

OTHER PUBLICATIONS

Invitation to Pay Additional Fees mailed Dec. 7, 2021, in connection with International Patent Application No. PCT/EP2021/077686, 9 pgs.

Office Action issued in Chinese Patent Application No. 201880023361.4 mailed on Mar. 3, 2021.

International Search Report and Written Opinion mailed Jun. 12, 2018 in International Application No. PCT/EP2018/055899.

International Search Report and Written Opinion mailed Oct. 7, 2021, in connection with International Patent Application No. PCT/EP2021/067500, 10 pgs.

Extended European Search Report mailed Feb. 2, 2024 in connection with European Patent Application No. 23206839.5, filed Oct. 30, 2020, 6 pgs.

* cited by examiner

IMPLANTATION TOOL FOR AN INTERPHALANGEAL IMPLANT

CROSS-REFERENCE TO RELATED APPLICATIONS

This application is a National Stage under 35 U.S.C. 371 of International Patent Application No. PCT/EP2021/077686, filed Oct. 7, 2021, which claims the benefit of priority to European Patent Application No. 20204941.7, filed Oct. 30, 2020; the disclosures of all of which are incorporated herein by reference in their entireties.

TECHNICAL FIELD

The present invention relates to a tool for implanting an interphalangeal implant, an interphalangeal implant retainer for use with the implantation tool, and a method for preparing the tool for an implantation of an interphalangeal implant.

BACKGROUND OF THE INVENTION

Functional disorders of interphalangeal joints such as finger joints are frequently caused by arthritis. One of the most common forms of arthritis is arthrosis. This disease leads to wear and tear of the joint cartilage, which in turn results in an incorrect loading of the joint and further deterioration of the joint surfaces. A patient experiences this deterioration in form of a painful restriction of movement or even elimination of the joint's function.

Dysfunctions of an interphalangeal joint can also result from injury, e.g., luxation of the joint or fracture of the joint. Particularly a joint fracture commonly leads to post-traumatic arthrosis of the joint with the above noted consequences.

To eliminate pain occurring due to such functional disorders, interphalangeal implants have been developed that address this problem by replacing the affected interphalangeal joint.

One type of these interphalangeal implants is a finger arthrodesis implant. This type of implant removes the finger joint including its function. As a result, the connection between the two phalangeal bones adjacent to the former native joint is stiff. Although this makes the pain disappear, it also means the loss of the joint's movability for the patient.

Another way to eliminate such pains is to implant a finger joint implant. Such a finger joint implant allows to at least partially keep the joint's movability so that a patient may still perform at least simple tasks such as holding a pen.

More recently, there are finger joint implants available that do not require luxation of the native finger joint during surgery (cf. EP 1 096 906 A1). As a result, the extensor tendon apparatus, the two flexor tendons and one of the collateral ligaments of the joint can be preserved, which prevents a subsequent impairment of the finger implant's function. In addition, part of the bone tissue that had previously been sacrificed for the implantation of finger joint implants can be maintained (cf. DE 690 02 159 T2 and DE 103 54 601 B3).

One of the reasons for the improved performance of this type of an interphalangeal joint implant is the surgical procedure which avoids the aforementioned disadvantages. In this procedure, the interphalangeal joint implant can be implanted laterally into a recess that has been created at the position of the interphalangeal joint to be replaced. This has been found to considerably simplify the implantation procedure.

SUMMARY

The inventors' objective was in particular the enhancement of handling and implanting these interphalangeal implants. It was particularly an objective to simplify the implantation procedure, thereby improving the implantation result and accelerating the mobilization of the patient.

Further, it has been an objective to avoid direct contact of personnel, such as medical staff, with the interphalangeal implant before and during the surgical procedure in order to prevent contamination of the implant.

Yet another objective has been, to reduce the number of parts that need to be handled during implantation.

As a response to these objectives, the present disclosure provides a tool for implanting an interphalangeal implant, an implant retainer for an interphalangeal implant, and a method for preparing a tool for an implantation of an interphalangeal implant as defined in the subject matter of the independent claims. The claims dependent thereon specify preferred embodiments.

The tool for implanting an interphalangeal implant comprises a limb support for supporting a phalangeal limb, a driving rod, wherein the driving rod is movable for moving an interphalangeal implant towards the limb support, and an actuation mechanism for actuating the driving rod.

The limb support preferably supports a lateral side of the phalangeal limb. The limb support particularly provides support for a finger or a toe when inserting the interphalangeal implant into a prepared cavity of adjacent phalangeal bones. In other words, the limb support allows for placement and support of a limb to be treated at a predetermined position and in a predetermined orientation. This enhances the precision of guiding the interphalangeal implant into this limb.

The driving rod of the implantation tool is arranged for pushing the interphalangeal implant towards the limb support and into the implantation site within the bone tissue. For this reason, the driving rod is movable, in particular slidable. Preferably, the driving rod is (only) actuated to perform a lengthwise movement, i. e. a movement in which the rod performs a translatory movement.

For actuating the driving rod, the actuation mechanism is in engagement with the driving rod. The actuation mechanism provides for a controlled movement of the interphalangeal implant into a bone cavity that has been prepared in adjacent phalangeal bones. This may particularly be achieved using a mechanical linkage or transmission.

The interphalangeal implant may be an interphalangeal joint or an interphalangeal arthrodesis.

Further, the implantation tool preferably comprises an implant guiding means for guiding the interphalangeal implant towards the limb support.

On top of the guidance provided by the driving rod, the implant guiding means allows for additional control and precision of the movement of the interphalangeal implant into the implantation site. In other words, the implant guiding means serves to guide the interphalangeal implant into the implantation site while the driving rod moves the implant towards the limb support. Consequently, the guidance and movement of the interphalangeal implant are generally achieved by separate structural features of the implantation tool, allowing for an enhancement of the control of the implant's movement during implantation.

The implant guiding means is preferably arranged between the driving rod and the limb support and is even more preferably arranged to hold the implant. Further, the implant guiding means preferably acts in parallel to the driving rod.

It is particularly preferred that the implant guiding means comprises a female guide member and a male guide member, wherein the female guide member has an aperture or hole that on one side faces the limb support and on the opposite side faces the male guide member. The male guide member preferably has a pushing portion dimensioned to fit through the aperture of the female guide member.

Consequently, the male guide member preferably serves to push the interphalangeal implant through and out of the aperture of the female guide member towards the limb support in order to push the implant into the implantation site that has previously been prepared for the interphalangeal implant.

Preferably, the female guide member is designed for guiding the interphalangeal implant. More specifically, the aperture of the female guide member is preferably shaped and dimensioned to be at least partly in contact with the interphalangeal implant while the male guide member pushes the implant through the aperture of the female guide member, i. e. in the depth direction of the aperture. Such a configuration provides an enhanced guidance for the interphalangeal implant before and while the implant enters the implantation site of the limb supported by the limb support.

The male guide member is arranged for being driven by the driving rod, in particular by being in contact or in engagement with the driving rod. The interaction between the male guide member and the driving rod is preferably an engagement that allows for pushing the male guide member towards the limb support and/or pulling the male guide member away from this support.

The engagement may be configured so that the male guide member is engageable with and preferably disengageable from the driving rod. Preferably, the engagement is configured to allow for an adaptation of the relative orientation between the driving rod and the male guide member. In other words, the angle between the driving rod and the male guide member may be adjustable. Such an adjustment allows to correct the orientation of the implant relative to the limb during insertion into the implantation site.

Alternatively, the male guide member may be fixed to the driving rod or may be integrally formed with the driving rod.

Further, the limb support may be mounted to the tool so as to allow for an adjustment of its orientation relative to the longitudinal axis of the driving rod. This also allows for a correction of the relative orientation between implant and limb.

The female guide member and/or the male guide member preferably comprises an implant holder for holding the interphalangeal implant, wherein the implant holder is preferably configured to hold the interphalangeal implant via an interphalangeal implant retainer.

The implant holder for directly or indirectly (e. g. via the interphalangeal implant retainer) holding the interphalangeal implant allows for preventing contact with the implant after the implant has been loaded into the implantation tool. Consequently, the implant holder supports the objective to prevent unnecessary contact with the implant and therefore facilitates keeping the implant sterile. While the implant holder holds the interphalangeal implant, the implant is secured and prevented from falling off the implantation tool.

Advantageously, the implant holder may also be configured to keep a relative position between the female guide member and the male guide member during a movement of the male guide member into the female guide member, i. e. to keep the relative position perpendicular to the translatory movement of the driving rod constant). As a result, the implant holder is able to prevent a misalignment between the male guide member and the female guide member.

The implant holder is preferably formed as two pins. The pins may be fixed to the female guide member. The two pins are even more preferably arranged on opposite sides of the aperture of the female guide member. Accordingly, the pins are arranged on opposite sides of the pushing portion of the male guide member, wherein the male guide member may comprise corresponding holes for slidably receiving these pins. The holes are particularly dimensioned so that they are in contact with the pins and allow for a reciprocal relative movement of the pins along the holes.

Holding the interphalangeal implant via an interphalangeal implant retainer has the advantage that no contact is necessary when mounting the interphalangeal implant to the implantation tool. The implant retainer may also serve as part of a transport means for providing or delivering the interphalangeal implant before surgery (e. g. to a clinic or a hospital). Further, employing an implant retainer, such as an implant retainer as defined further below, allows for handling the interphalangeal implant as a single piece. In other words, the interphalangeal implant can be handled as a whole instead of as multiple small parts. Consequently, an implant retainer enhances and simplifies handling the interphalangeal implant.

Preferably, the female guide member includes a limb abutment side, wherein the limb abutment side is preferably formed as at least two contact surfaces protruding from the female guide member towards the limb support, the at least two contact surfaces being even more preferably arranged on opposite sides of the female guide member aperture.

The limb abutment side has the advantage to provide a defined contact with a limb. In particular when being formed as two or three separate contact surfaces, the female guide member is generally provided with a mechanically defined two-point or three-point contact with the limb, respectively. Accordingly, the limb to be treated can be securely fixated between the contact surfaces and the limb support.

In order to prevent the limb from sliding of the limb support during fixation, the limb support may have a longitudinal recess for receiving and supporting the limb that is oriented transverse to the longitudinal axis of the driving rod. Even more preferably, the longitudinal recess is tapering from a maximum width towards both ends of this recess to a width smaller than the maximum width.

Further, if at least two contact surfaces are arranged on opposite sides of the female guide member's aperture, the contact surfaces protruding from the female guide member's surface cause a gap between this surface and a limb supported by the limb support. This gap functions as a window in a direction perpendicular to the aperture so that it is possible to observe the interphalangeal implant while it is inserted into the cavity for receiving the implant.

Preferably, the male guide member further comprises a driver engagement portion for a releasable engagement of the driving rod.

The releasable engagement of the driving rod allows for a placement of the interphalangeal implant, preferably held by an implant retainer, between the female guide member and the male guide member before bringing this pre-assembly with the driving rod of the implantation tool into engagement.

As already indicated above, the engagement between the male guide member (more specifically, the driver engagement portion) and the driving rod is preferably configured to allow for slight rotational adjustments (e. g. a maximum of ±20°, ±15°, ±10°, ±5° or ±3°) of the male guide member in relation to the longitudinal direction of the driving rod. As a result, it is possible to adapt the orientation of the male guide member in relation to the shape of the limb and, in particular, the implantation site.

Preferably, the actuation mechanism is configured to transform a rotatory movement into a translatory movement.

The transformation of a rotatory movement into a translatory movement provides an enhanced control of the driving rod's movement and, thus, of the interphalangeal implant into the implantation site. Even more preferably, the transformation of the rotatory movement into the translatory movement includes a reduction to further facilitate the control and precision of the driving rod's movement.

The actuation mechanism may further comprise a support handle and a movable handle, wherein the movable handle is rotatable about a pivot axis. The support handle and the movable handle are preferably arranged in relation to each other so that they can be operated by a hand of a user.

This actuation mechanism advantageously allows a user (e.g., a surgeon) to actuate the actuation mechanism with a single hand. Consequently, the other hand is free and may be used to hold the implantation tool in position for guiding the interphalangeal implant into the prepared cavity of the implantation site. The user may operate the actuation mechanism by pulling the movable handle with his or her fingers while the palm of the hand is supported by the support handle. Due to the fine motor skills provided the fingers of the user, this arrangement of the actuation mechanism allows for a precise control of the implant's insertion.

Preferably, the actuation mechanism further comprises an engagement plate and the driving rod passes through a hole in the engagement plate, wherein the hole in the engagement plate is dimensioned so that tilting the engagement plate relative to the driving rod when starting from an initial position causes the driving rod and the engagement plate to be engaged in a driving state, and wherein upon actuation of the movable handle, the moveable handle first pushes and tilts the engagement plate to assume the driving state so that further movement of the movable handle pushes the driving rod via the engagement plate towards the limb support.

In other words, in the driving state, the driving rod and the engagement plate are locked to each other in an axial direction so that tilting the engagement plate to one side causes the driving rod to move into this direction (i.e., towards the limb support).

This configuration provides a simple and reliable mechanism for causing a driving engagement between the engagement plate (i. e. the movable handle) and the driving rod. As a result, the components of this mechanism are easy to clean and easy to disinfect.

Preferably, a return biasing means is arranged to bias the engagement plate towards the initial position so that releasing the movable handle causes the engagement plate to return to its initial position.

Consequently, the return biasing means causes the engagement plate to tilt backwards so that the movable handle preferably moves back to its initial position. The engagement plate tilting backwards (i.e., away from the limb support) releases the engagement between the engagement plate and the driving rod and allows the engagement plate to return to its initial position. Accordingly, the movable handle may be actuated several times for driving an interphalangeal implant towards the limb support.

The return biasing means is preferably an elastic element, such as a spring, and even more preferably surrounds the driving rod (i.e., the driving rod is insertable into the elastic element). The return biasing means has as a function to disengage the engagement plate from the driving rod if no external force is applied to the engagement plate or the movable handle.

Preferably, the actuation mechanism further comprises an engagement biasing means and a retainment plate, the retainment plate including a retainment hole. The driving rod is movable through the retainment hole in a disengaged state.

Further, the retainment hole may be dimensioned so that the retainment plate and the driving rod are engaged in a retainment state if the retainment plate is tilted relative to the driving rod, and the engagement biasing means biases the retainment plate to be tilted relative to the driving rod.

The engagement biasing means allows for keeping the retainment plate tilted in a perpendicular orientation to the driving rod (i.e., keep the longitudinal axis of the retainment hole inclined to the longitudinal axis of the driving rod) so that the retainment plate and the driving rod keep being engaged if no external force is applied that would move the driving rod towards the limb support. The engagement plate is particularly tilted away from the limb support. As a result, the retainment plate prevents an unintended translatory movement of the driving rod in its longitudinal direction away from the limb support. i. e. in a proximal direction. At the same time, the engagement plate allows for a translatory movement towards the limb support, i. e. in a distal direction of the implantation tool. Such a movement tends to tilt the retainment plate towards a disengaged orientation. In other words, the biased inclination between the retainment plate and the driving rod causes the driving rod to be only movable in a distal direction towards the limb support.

In the initial position of the engagement plate, the retainment plate and the driving rod are preferably engaged in the retainment state. In the driving state of the engagement plate and the driving rod, the retainment plate and the driving rod are preferably able to move relative to each other (i. e. there is no engagement in the distal direction).

In other words, the engagement plate on the one hand and the retainment plate on the other hand have different and mutually complementary purposes. More specifically, the retainment plate may prevent the driving rod from unintentionally moving in a direction away from the limb support whereas the engagement plate allows for moving the driving rod in a direction towards the limb support. This provides a consistent and particularly controlled movement of an interphalangeal implant towards the limb support.

Also in this configuration, the retainment plate allows for essentially keeping up the compressive force of the driving rod applied to the implant during insertion, while the engagement plate returns to its initial position for the next actuation of the driving rod to push the interphalangeal implant further towards the limb support (i.e. into the implantation site). In other words, the interplay between the engagement plate and the retainment plate allows for a repeated actuation of the actuation mechanism in order to drive the driving rod towards the limb support without the driving rod being able to significantly move backwards in between actuations.

The disclosure further provides an interphalangeal implant retainer for retaining an interphalangeal implant, wherein the implant retainer is for being used with an implantation tool, in particular an implantation tool as disclosed above. The implant retainer comprises a jig part. The jig part has a plate-shape, includes an implant aperture for retaining an interphalangeal implant, and is preferably configured to be mounted to the implantation tool.

The implant retainer facilitates handling of the interphalangeal implant due to the jig part of the implant retainer. This configuration of an implant retainer particularly prevents direct contact of a user with the implant. As previously noted, the jig part is preferably also used as a means to mount the interphalangeal implant to the implantation tool via the implant holder. Thus, there is also minimal contact to the implantation tool. The jig part also has the advantage of a user being able to handle the pre-assembled interphalangeal implant as one piece instead of having to handle and insert sections of an implant one after the other. As a result, the time needed for implantation is reduced.

In order to be mounted to the implantation tool, the jig part is preferably provided with a holding means that is configured to correspond to the implant holder of above described implantation tool. Accordingly, the holding means is preferably formed as at least two through holes that are engageable with at least two pins of the implant holder, respectively. The at least and in particular two through holes are even more preferably arranged on opposite sides of the implant aperture. The holding means may also be used for handling the interphalangeal implant prior installation to the implantation tool.

The implant aperture is dimensioned to hold the implant, in particular by a friction and/or a form fit (preferably a releasable snap fit). In other words, the interphalangeal implant is secured to the jig part so that it cannot fall out of the implant aperture, e. g. due to gravity alone. Further, the jig part protects the interphalangeal implant during handling if it is subjected to an external impact.

Preferably, the interphalangeal implant retainer comprises an implant casing defining an implant receiving space. The implant casing includes a jig retaining structure for releasably engaging a casing retaining structure of the jig part, wherein the engagement between the jig retaining structure and the casing retaining structure is preferably configured as a form fit connection, in particular a releasable snap-fit connection.

Such a casing of the interphalangeal implant retainer further enhances protection of an interphalangeal implant retained therein via the jig part. Also, the casing may already be used for packaging the interphalangeal implant to be send to the clinic, where surgery takes place. For example, the interphalangeal implant retainer may protect an interphalangeal implant on its transport from a production site to a patient. It may then be taken out of the implant casing, in particular for mounting the jig part holding the interphalangeal implant to the implantation tool, i. e. to prepare the tool for the implantation of the interphalangeal joint.

The jig retaining structure of the implant casing and the casing retaining structure provided to the jig part further improve the protective function of the casing by securing the jig part holding an interphalangeal implant to the casing. If a releasable snap-fit connection between the implant casing and the jig part is used, the interphalangeal implant located within the aperture of the jig part is on the one hand safely kept inside the casing and may on the other hand easily be taken out by releasing the snap-fit connection.

The casing retaining structure may be a slit or a groove, wherein the groove may be arranged on an inner side and/or an outer side of the implant casing.

The present disclosure further provides a method for preparing an implantation tool, in particular an implantation tool as described above, for an implantation of an interphalangeal implant. The method comprises the steps of providing an implant retainer, in particular an implant retainer with a configuration of above, that retains the interphalangeal implant; bringing a holding means of the implant retainer into engagement with an implant holder of the implantation tool; and actuating an actuation mechanism of the implantation tool for bringing a male guide member of the implantation tool into abutment with the interphalangeal implant.

If the implant retainer keeps the interphalangeal implant within the jig part, which is in turn located within an implant casing, the jig part is taken out of the implant casing before being brought into engagement with an implant holder of the implantation tool.

Once mounted to the implantation tool, the interphalangeal implant may be pushed out of the jig part by actuating the actuation means of the implantation tool so that the driving rod is moving towards the limb support into contact with the interphalangeal implant. As a result, the interphalangeal implant is moving out of the jig part's aperture and is inserted into adjacent interphalangeal bones of a limb while the limb is supported by the limb support. Accordingly, the limb support counters the force that the driving rod exerts to the interphalangeal implant.

In this manner, the implantation tool greatly facilitates the insertion of an interphalangeal implant into a limb for placing the implant at an implantation site, i.e. a cavity prepared within the bone tissue of the limb. Further, and as described above, this configuration of an implantation tool and an implant retainer allows for a safe and contact-free handling of the implant before and during surgery.

BRIEF DESCRIPTION OF THE DRAWINGS

The following figures illustrate preferred embodiments of the present invention. These embodiments are not to be construed as limiting but merely for enhancing the understanding of the invention in context with the following description. In these figures, same reference signs refer to features throughout the drawings that have the same or an equivalent function and/or structure. It is to be noted that a repetitive description of these components is generally omitted for reasons of conciseness.

DETAILED DESCRIPTION

In the following, preferred embodiments and their modifications of an implantation tool for an interphalangeal implant, an implant retainer, and a method for preparing the implantation tool for an implantation are described under reference to the accompanying figures.

An interphalangeal implant is to be understood as an implant that is inserted between two adjacent phalangeal bones using the implantation tool of the present disclosure. In other words, an interphalangeal implant replaces an interphalangeal joint of a hand or a foot. Most commonly, an interphalangeal implant serves as a replacement for a proximal interphalangeal joint of a patient's hand. However, it may also replace a proximal interphalangeal joint of a patient's foot. Similarly, an interphalangeal implant may replace a distal interphalangeal joint of a patient's hand or foot. Nonetheless, other joints may be envisaged for replacement as long as it is possible to provide lateral access for the implantation of the interphalangeal joint. For example, the metacarpophalangeal joint of a thumb or a small finger allows for such a lateral access.

As already described above, the interphalangeal implant may be configured as an interphalangeal joint implant that replaces a native joint or acts as an interphalangeal arthrodesis implant.

An interphalangeal joint implant is generally configured as a hinge joint. It may further have a configuration that allows for comparatively small movements in rotational (supination/pronation) and/or translational directions (compression/distraction) in order to enhance the adaption of the interphalangeal joint implant to the kinematic environment of a patient. This kinematic environment is, for example, defined by the arrangement of tendons and muscles. As a result, the interphalangeal joint implant basically functions like a native joint. For a more detailed description of an interphalangeal joint implant that may be implanted using the implantation tool of the present disclosure, it is referred to the European application EP 20 182 547.8, which is hereby incorporated by reference.

In contrast to an interphalangeal joint implant, an interphalangeal arthrodesis implant locks the interphalangeal joint at a predetermined angle between the two adjacent phalangeal bones. For a detailed description of an interphalangeal arthrodesis implant, it is referred to WO 2018/188861 A1, which is hereby incorporated by reference.

Both types of interphalangeal implants preferably comprise a first anchoring section 11 and a second anchoring section 12 that even more preferably extend wing-like (i.e., in the form of generally flat elongated plates) from a central section 14 (see FIG. 1) to the distal end and proximal end of the implant. In an implanted state, the central section 14 is to be located between the interphalangeal bones, i.e., at the location of the native joint, whereas the anchoring sections fix the interphalangeal implant to the adjacent interphalangeal bones.

Figure 1:
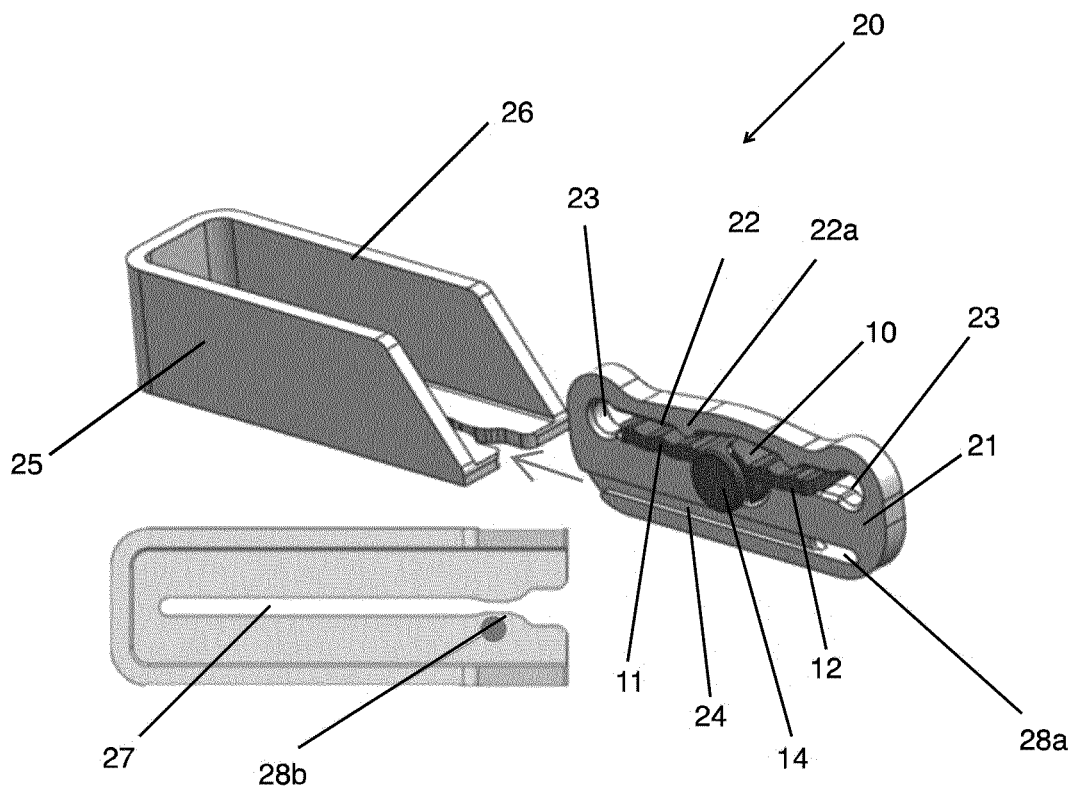
FIG. 1 illustrates an interphalangeal implant that is accommodated in an implant retainer and an implant casing according to an embodiment of the disclosure.

Turning to the figures, FIG. 1 is a three-dimensional view of an embodiment of an implant retainer 20 comprising a jig part 21 and an implant casing 25. The implant casing 25 is shown in FIG. 1 as a three-dimensional view during assembly with a jig part 21. FIG. 1 also illustrates the implant casing 25 in a plan view.

The plate-like jig part 21 includes an implant aperture 22 formed as a through-hole for receiving an interphalangeal implant 10. The implant aperture 22 is dimensioned to hold the interphalangeal implant 10 by friction and/or by a form fit (e.g., a snap-fit). Accordingly, the circumferential shape of the implant aperture 22 preferably corresponds to the contour of a cross-section of the interphalangeal implant 10 perpendicular to the direction of insertion of the implant 10 into the implant aperture 22. In the exemplary embodiment of FIG. 1, this cross-section is a longitudinal cross-section of the interphalangeal implant 10 perpendicular to the joint axis of the implant's joint section in the central section 14 of the implant 10.

In the exemplary embodiment of a jig part 21, the jig part 21 has multiple retaining protrusions 22a (preferably at least three) that extend into the implant aperture 22 from the surrounding edge of the implant aperture 22 (i. e. perpendicular to the depth of the implant aperture 22). These retaining protrusions 22a may retain the interphalangeal implant 10 within the aperture 22 by friction (in a direction perpendicular to the implant aperture 22, i. e. in the depth direction of the aperture 22) and/or by a form fit (in the directions parallel to the cross-section of the implant aperture 22, i.e., perpendicular to the depth direction of the aperture 22).

Figure 2:
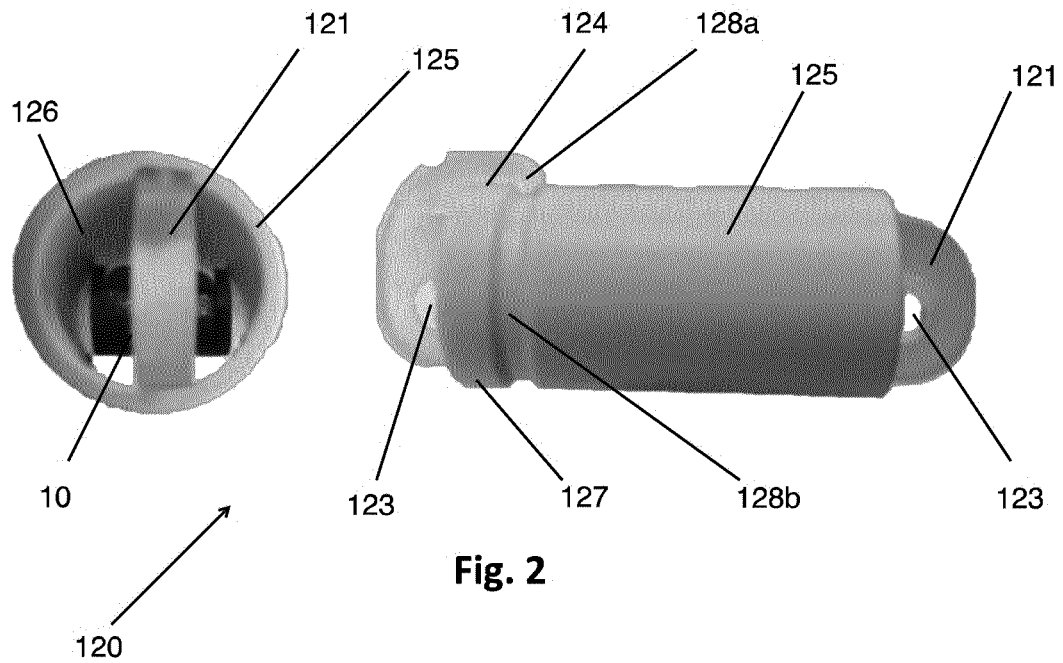
FIG. 2 illustrates an interphalangeal implant that is accommodated in an implant retainer and in an implant casing according to another embodiment of the disclosure.

The jig part 21 further may include a holding means 23. As shown in FIG. 1, the holding means 23 may be formed as through holes that are located on opposite sides of and extend parallel to the implant aperture 22. Although the holding means 23 of the exemplary embodiment shown in FIG. 1 is illustrated as forming an integral part of the implant aperture 22, the through holes of the holding means 23 may also be formed as separate holes. As shown in FIGS. 1 and 2, the through holes of the holding means 23 are preferably formed on the sides of the proximal and distal ends of the interphalangeal implant 10.

Further, the jig part 21 may further include a casing retaining structure 24. In the exemplary embodiment of FIG. 1, the casing retaining structure 24 comprises two grooves. The two grooves preferably extend in the longitudinal direction of the jig part 21 (or longitudinal direction of the cross-section of the implant aperture 22, i. e. the longitudinal direction of the interphalangeal implant 10 from the proximal end to the distal end) and are formed on opposite sides of the plate like jig part 21 (i.e., opposite sides of the aperture 22).

The casing retaining structure 24 of the jig part 21 is configured to engage a jig retaining structure 27 of the implant casing 25. In FIG. 1, the jig retaining structure 27 of the implant casing 25 is formed as a slit, wherein the sidewalls of the slit are engageable with the opposite grooves of the casing retaining structure 24. Engagement and disengagement is performed by a sliding or translatory movement of the jig part 21 and the implant casing 25 relative towards and away from each other, respectively. In other words, the casing retaining structure 24 of the jig part 21 allows the jig part 21 to slide into and along the slit of the jig retaining structure 27 of the implant casing 25.

As illustrated in FIG. 1, the casing retaining structure 24 of the jig part 21 and the jig retaining structure 27 of the implant casing 25 may further comprise snap-fit features that are preferably brought into engagement once the jig part 21 is fully inserted into the casing 25.

In the exemplary embodiment of FIG. 1, the engaging structure of the snap-fit feature is formed on the side of the implant casing 25 as protrusions 28b that form a narrowed down portion at the entrance of the slit and as a recess 28a (in particular a through hole) at a corresponding position of grooves of the jig part 21. The recess 28a is configured to receive the protrusions 28b that form the narrowed down portion of the slit. Although the snap-fit feature shown in FIG. 1 comprises two pairs of engaging structures (two protrusions extending into the slit and two recesses formed on opposite sides of the plate-like jig part 21), in general at least one pair of engaging structures may be provided.

With the jig part 21 inserted into the implant casing 25, the interphalangeal implant 10 can be received in an implant receiving space 26 of the implant casing 25. The implant receiving space 26 is a space that is at least partially enclosed. The sides of the implant receiving space 26 are at least dimensioned or configured so that independent of the orientation of the implant casing 25, a mounted interphalangeal implant 10 cannot get in contact with a flat surface the implant casing 25 is placed on. As shown in FIG. 1, this may be achieved by an implant casing 25 having a wall partly surrounding a base, wherein the jig retaining structure 27 is comprised in the base.

Further, an implant casing 25 with an implant receiving space 26 configured this way, enhances the use of a vacuum sealed package. Since the packaging material (in particular a polymer film) is kept from being in contact with the interphalangeal implant 10 or the jig part 21, the packaging material is prevented from accidentally moving the jig part 21 out of the implant casing 25 while a vacuum is applied. Such an inadvertent movement may also or alternatively be prevented by providing above-described snap-fit features to the jig part 21 and the implant casing 25.

Preferably, the jig part 21 and/or the implant casing 25 are each integrally formed.

Another embodiment of an implant retainer is shown in FIG. 2. The implant retainer 120 of FIG. 2 has at least similar functional aspects and features like the implant retainer 20 illustrated in FIG. 1. Accordingly, a detailed description of such functional aspects and features is omitted and, instead, it is referred to the description of the previous embodiment of an implant retainer 20.

Similar to the previous embodiment of the implant retainer 20, the implant retainer 120 also comprises a plate-like jig part 121 with an implant aperture (not shown) and a holding means 123.

However, the implant casing 125 of the implant retainer 120 has a tubular form for receiving an interphalangeal implant 10 inserted into the jig part 121. A jig retaining structure 127 is formed by a portion of the tubular implant casing 125 extending from one end of the implant casing 125 towards the other end of the implant casing 125 in the longitudinal direction.

Similar to the implant casing 25, here, the jig part 121 comprises a casing retaining structure 124 that is formed as a longitudinal slit that extends starting at a distance from an end of the jig part 121 in the longitudinal direction of the jig part 121 and has an entrance that is opening towards the other end in the longitudinal direction of the jig part 121.

At the entrance of the slit, the slit may be narrowed down at least on one side by a protrusion extending from a sidewall of the slit (cf. FIG. 2). This protrusion of the casing retaining structure 124 forms a snap-fit feature 128a that is engageable with a recess of the jig retaining structure 127 of the implant casing 125. This recess corresponds to the protrusion of the snap-fit feature 128a and embodies a snap-fit feature 128b of the implant casing 125. The snap-fit feature 128b is located at the end of the jig retaining structure's portion that is located along the implant casing 125 (i.e., not at the end).

As shown in FIG. 2, the recess representing the snap-fit feature 128b is preferably formed as a circumferential groove in the outer surface of the implant casing 125.

For assembly, the interphalangeal joint 10 is inserted into the aperture (not shown) of the jig part 121. Then, the jig part 121 is inserted into and along the longitudinal direction of the tubular implant casing 125. During insertion, the slit of the casing retaining structure 124 receives the portion of the wall of the tubular implant casing 125 representing the jig retaining structure 127 until the snap-fit features 128a, 128b engage each other (i.e., the protruding portion snaps into the recess).

As will be described in the following, the interphalangeal implant 10 may be mounted to an implantation tool 30 via the implant retainer 20, 120 after removal of the implant casing 25, 125.

An implantation tool 30 for insertion of the interphalangeal implant 10 into a limb of a patient will now be explained in more detail under reference to FIGS. 3 to 6.

Figure 3:
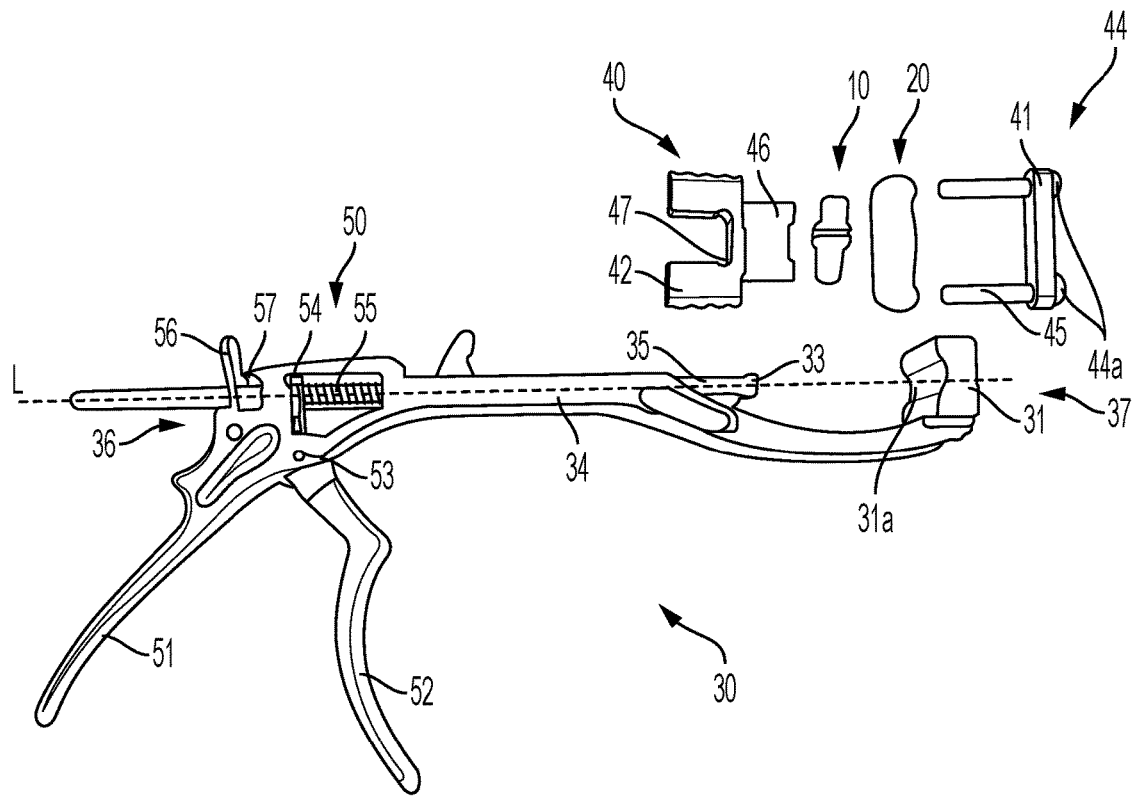
FIG. 3 illustrates an embodiment of an implantation tool, an interphalangeal implant and an implant retainer in a disassembled arrangement according to an exemplary embodiment of the disclosure.

FIG. 3 is a side view of an implantation tool 30. This figure also shows an exploded plan view of an interphalangeal implant 10, an implant retainer 20, and an implant guiding means 40 to be mounted to the implantation tool 30 in order to prepare the implantation tool 30 for the implantation of the interphalangeal implant 10.

Figure 6:
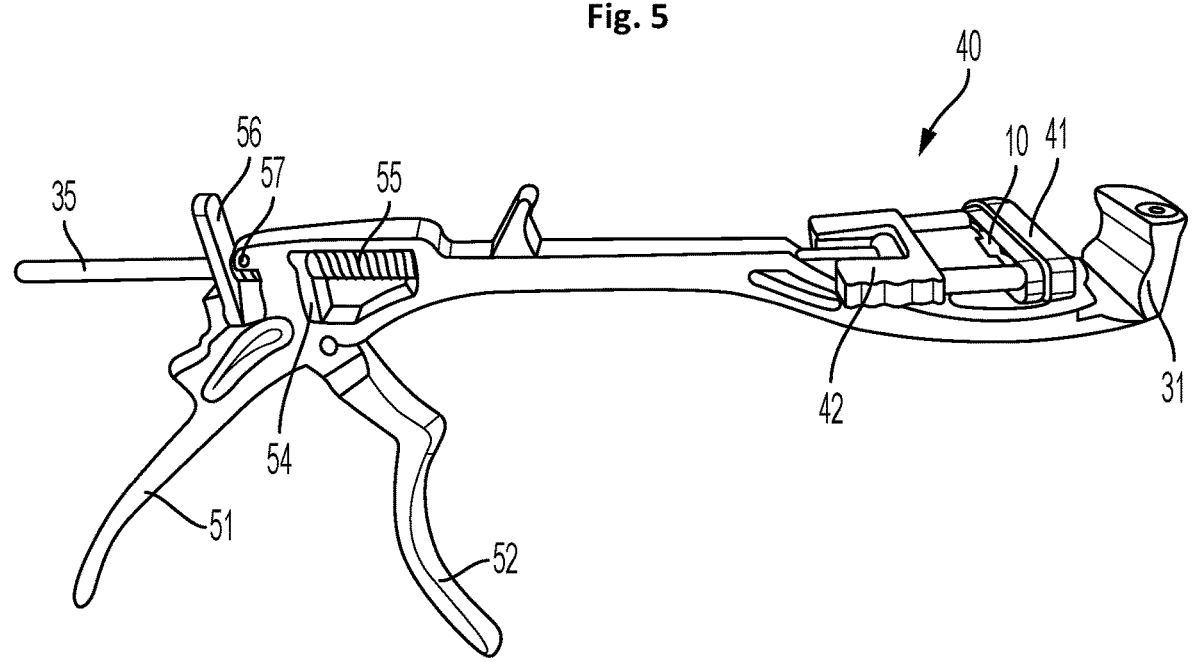
FIG. 6 illustrates the implantation tool in a pre-assembled condition and prepared for the implantation of an interphalangeal implant.

Turning to FIGS. 3 and 6, the implantation tool 30 comprises a chassis 34 and a proximal end 36 and a distal end 37. An actuation mechanism 50 for actuating the implantation tool 30 in order to insert an interphalangeal implant 10 into a prepared cavity within adjacent interphalangeal bones (not shown) is located in a proximal section of the implantation tool's chassis 34 at the proximal end 36. The distal end of the chassis 34 is provided with a limb support 31 for placing a limb of a patient during surgery.

A driving rod 35 is coupled to the actuation mechanism 50 at the proximal end and extends in a longitudinal direction L along the chassis 34 towards the limb support 31. As illustrated in FIG. 3, the distal end of the driving rod 35 may be provided with a male guide member engagement portion 33 that will be described in more detail further below. the driving rod 35 is movable along the longitudinal direction L.

The limb support 31 is preferably formed with a longitudinal supporting groove 31a (longitudinal recess). The groove 31a facilitates placement of a limb to be treated and prevents the limb from slipping off the limb support 31 in a perpendicular direction of said groove 31a. The groove 31a may have a constant cross-section. Preferably, the groove 31a has a variable cross-section for providing an enhanced support for a limb. In particular, the groove may taper from a cross-section having a maximum width towards both ends of the groove 31a to a cross-section having a width smaller than the maximum width. Thus, the course of the cross-section of the groove 31a generally corresponds to the course of the cross-section of a limb, which has a smaller cross-section at the interphalangeal bones compared to the cross-section at the interphalangeal joint.

Consequently, the limb support 31 is able to securely hold a limb during a surgical procedure for implanting an interphalangeal implant 10. Further, the limb support 31 supports the limb while the interphalangeal implant 10 is pushed into the bone tissue of the limb in order to establish a press-fit between the interphalangeal implant 10 and the adjacent interphalangeal bones of a patient. In other words, the limb support 31 acts as a counter-bearing for the pressure applied via the driving rod 35.

Figure 4:
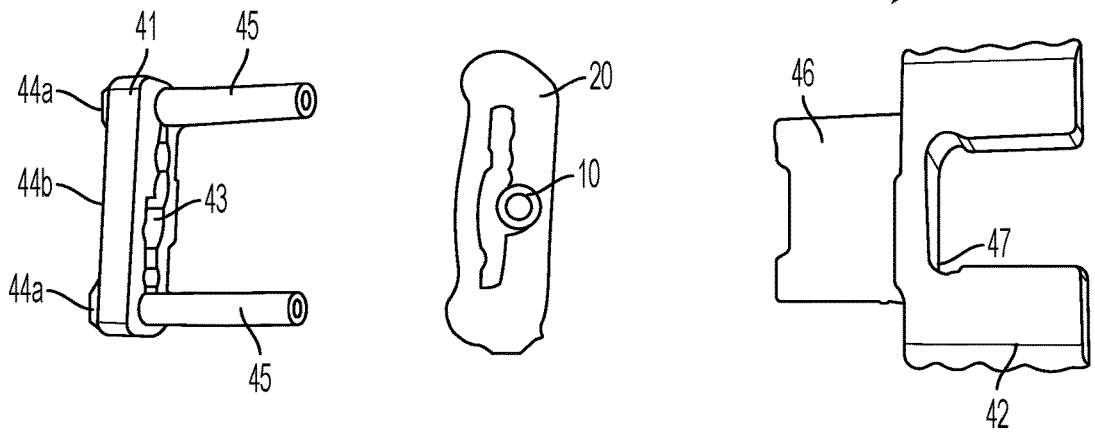
FIG. 4 illustrates an exploded view of a guiding means of the implantation tool and an interphalangeal implant held by an implant retainer according to an embodiment of the disclosure.

During implantation, the interphalangeal implant 10 is supported and guided by a guiding means 40. The guiding means 40 is placed at the distal end of the driving rod 35. As shown in FIGS. 3 and 4, the guiding means 40 comprises a male guide member 42 and an implant holder 45. The male guide member 42 and the female guide member 41 can be coupled to each other while allowing for a translatory movement relative to each other along the longitudinal direction of the driving rod 35.

By way of example, the male guide member 42 illustrated in FIGS. 3 to 6 comprises two holes (not shown) formed on opposite sides of the male guide member 42 and extending parallel to the driving rod 35 (i.e., along the longitudinal direction L). The holes are configured to interact with an implant holder 45 of the female guide member 41.

As shown in FIGS. 3 and 4, the implant holder 45 may in turn be formed as two pins that are located at opposite sides of the female guide member 41. The two pins are arranged at locations that correspond to the holes of the male guide member 42 and extend for insertion into these holes from the main body of the female guide member 41 towards the male guide member 42. This pin-hole configuration allows for a sliding engagement between the female guide member 41 and the male guide member 42 in the longitudinal direction of the pins and holes while the implant guiding means 40 is mounted to the implantation tool 30 (i.e. in the longitudinal direction).

The male guide member 42 further comprises a male pushing portion 46 that is dimensioned to pass through a female guide member aperture 43 of the female guide member 41. As previously described, the female guide member aperture 43 is preferably arranged in between the implant holder, e.g., the two pins, of the female guide member 41.

The female guide member aperture 43 is formed as an elongated through hole that allows an interphalangeal implant 10 to pass through.

For an enhanced guidance of the interphalangeal implant 10, the female guide member aperture 43 may have a circumferential wall (i.e., a cross-section perpendicular to the depth of the aperture 43) that generally corresponds to the outer shape of the interphalangeal implant 10. In this manner, a correct orientation of the interphalangeal implant 10 may be ensured if the interphalangeal implant 10 is only able to pass through the female guide member aperture 43 when having a predetermined orientation. Even more preferably, the elongated female guide member aperture 43 is symmetrical in relation to a plane perpendicular to the cross-section and arranged in the center of the elongated female guide member aperture 43.

Figure 5:
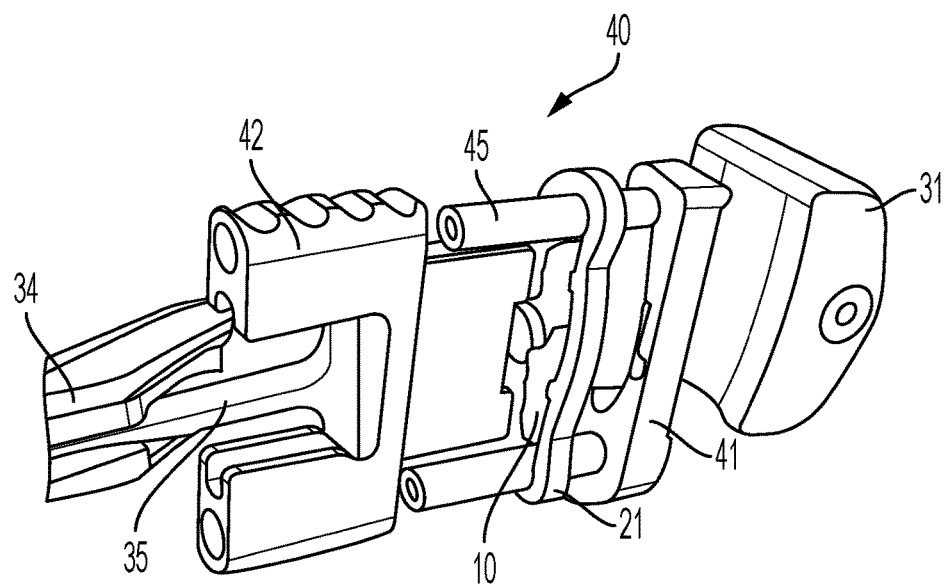
FIG. 5 shows the guiding means of FIG. 4 placed in the implantation tool for an implantation of the interphalangeal implant.

As particularly shown in FIGS. 4 to 6, the interphalangeal implant 10 is preferably held by the implant holder 45 of the female guide member 41 via an implant retainer 20 comprising a jig part 21 (the implant retainer 20 is only shown as an example and may be replaced by a different implant retainer such as the implant retainer 120 described above).

Accordingly, and as already described above, the implant retainer 20 and in in particular the jig part 21 of the implant retainer 20 is provided with a holding means 23 that may be formed as two through holes at opposite ends of the jig part 21. These two through holes slidingly interact with the two pins of the implant holder 45 so that the jig part 21 is held by and is movable relative to the female guide member 41 and the male guide member 42.

Thus, the implant holder 45 acts on the one hand as a holder for the jig part 21, which in turn holds the interphalangeal implant 10, and on the other hand as a guidance for the relative movement between the female guide member 41 and the male guide member 42.

For mounting the interphalangeal implant 10 to the implant guiding means 40, the interphalangeal implant 10 is initially inserted into the implant aperture 22 of the jig part 21 (as described above, this may already be the case while the interphalangeal implant is still packaged). Then, the interphalangeal implant 10 is mounted to the implant holder 45 of the female guide member 41 via the holding means 23 of the jig part 21.

If the interphalangeal implant is provided within an implant casing 25, the interphalangeal implant 10 arranged in the jig part 21 may have to be taken out of the casing 25 prior installation to the implantation tool 30 (cf. FIG. 1). Once the jig part 21 is mounted to the female guide member 41, the implant holder 45 is assembled to the male guide member 42, in particular via the previously described holes (in particular through holes).

This preassembly of the male guide member 42, the interphalangeal implant 10, the jig part 21 and the female guide member 41 is then mounted to the implantation tool 30. For this reason, the male guide member 42 preferably comprises at its proximal end a driver engagement portion 47 configured for an engagement with the driving rod 35.

Accordingly, the driving rod 35 comprises at its distal end a male guide member engagement portion 33. The driver engagement portion 47 and the male guide member engagement portion 33 are preferably formed so as to allow for a rotation within a predetermined range (for example ±20°, ±15°, ±10°, ±5° or ±3°). This ability to pivot allows for an adaptation of the orientation of the implant guiding means 40 and, thus, the interphalangeal implant 10, in accordance to a patient's limb that is placed on the limb support 31. In other words, the pivotable connection between the driving rod 35 and the male guide member 42 allows a correction of the implant's position and/or orientation during insertion.

As described above, the limb support 31 may also be pivotally supported on the chassis 34 of the implantation tool 30. This pivotable support may be provided in addition or alternatively to the pivotable engagement between the driver engagement portion 47 and the male guide member engagement portion 33. Likewise, the support of the limb support 31 may be able to rotate in an angular range of ±10°, ±5° or ±3°.

After the implant guiding means 40 is assembled to the implantation tool 30, the driving rod 35 may be actuated to perform a translatory movement in the distal direction of the implantation tool 34. This movement serves to drive and push the interphalangeal implant 10 via the pushing portion 46 of the male guide member 42 through the female guide member aperture 43.

For enhancing the control of this push-out movement, the female guide member 41 may be provided with (at least) two contact surfaces 44a. The contact surfaces 44a are configured to abut against the limb to be treated and provide on the one hand a defined two-point contact with the limb and on the other hand and implantation window 44b (cf. FIG. 4). As described above, the contact surfaces 44a protrude from the side of the female guide member 41 that faces the limb support 31. Preferably, the contact surfaces 44a are located at positions that are aligned with the pins forming the implant holder 45.

Further, orientation through holes (not shown) may extend from the contact surfaces through the female guide member 41 including the pins of the implant holder 45, i.e. each contact surface includes one orientation through hole. These orientation through holes are dimensioned to receive orientation pins (e.g. Kirschner wire) that are inserted into the interphalangeal bones of a patient's limb using a navigation method. Consequently, these orientation through holes enhance the positioning and guidance of the interphalangeal implant 10 during implantation.

As previously described, the implantation window 44b formed by the protruding contact surfaces 44a allows for a visual inspection of the implant's insertion into the limb of a patient.

Once the implant guiding means 40 is assembled with the implantation tool 30 (cf. FIGS. 5 and 6), the driving rod 35 may be actuated using the actuation mechanism 50, which will be described in more detail the following.

During actuation, the pushing portion 46 of the male guide member 42 gets into contact with the interphalangeal implant 10. Further, the implant guiding means 40 moves altogether towards a limb placed on the limb support 31 for treatment. Once the contact surfaces 44a abut the limb, the male guide member 42 continues being pushed by the driving rod 35 towards the limb support 31 while moving relative to the female guide member 41. As a result, the pushing portion 46 of the male guide member 42 pushes the interphalangeal implant 10 out of the implant retainer 20, through the implant aperture 22 of the female guide member 41, and presses the interphalangeal implant 10 into the prepared cavity of the interphalangeal bones within the limb.

The actuation mechanism 50 is preferably configured to transform a rotatory movement caused by a user of the implantation tool 30 into a translatory movement of the driving rod 35. Even more preferably, this transformation of a rotatory movement into a translatory movement includes a mechanical linkage and/or a transmission that enhances control using a reduction ratio. This reduction ratio transforms a relatively large rotatory movement into a smaller translatory movement. As a result, the reduction ratio enhances control of movement and at the same time the force available for pushing the interphalangeal implant 10 into the implantation site.

An example of an actuation mechanism that employs a reduction ratio is shown in FIGS. 3 and 6. In this exemplary embodiment, the rotary movement is applied by a user via a handle assembly. This handle assembly comprises a support handle 51 and a movable handle 52. The support handle 51 is fixed (preferably integral to) the chassis 34 of the implantation tool 30. The movable handle 52 is rotatable about a pivot axis 53. As shown in FIGS. 3 and 6, the support handle 51 and the movable handle 52 are arranged in the proximal section of the chassis 34. The handles enable a user to actuate the implantation tool 30 with a single hand, while the other hand may be used to assist in guiding and inserting the implant into a prepared bone cavity.

The user may operate the actuation mechanism 50 by pulling the movable handle 52 with his or her fingers while the palm of the hand is supported by the support handle 51. The fine motor skills of the fingers allow for a precise control during the implant's insertion. This precise control is also provided by the direct feedback of the actuation mechanism 50 to a user. In other words, the user is able to feel the resistance of insertion while pushing the interphalangeal implant 10 into a patient's limb.

For driving the driving rod 35 towards the limb support 31, the actuation mechanism 50 preferably comprises an engagement plate 54. The engagement plate 54 includes a through hole (not shown). In an assembled state, the driving rod 35 passes through this hole in the engagement plate 54.

The through hole or engagement hole in the engagement plate 54 is dimensioned in relation to the cross-section of the driving rod 35 so that a tilting movement of the engagement plate 54 relative to the driving rod 35 causes the driving rod 35 and the engagement plate 54 to be engaged, in particular by friction. As a result, the engagement plate 54 and the driving rod 35 assume a driving state.

In other words, the longitudinal axis of the through hole in the engagement plate 54 and the longitudinal axis L of the driving rod are inclined in relation to each other while the engagement plate 54 and the driving rod 35 are in the driving state, i. e. engaged. In contrast, the longitudinal axis of the through hole and the longitudinal axis L of the driving rod 35 being parallel causes the driving rod 35 and the engagement plate 54 to be disengaged.

In particular, tilting the engagement plate 54 causes the engagement plate 54 to get in contact with the driving rod 35 on opposite sides of the through hole, which extends throughout the engagement plate 54. These opposite sides are at a distance perpendicular to the tilting axis of the engagement plate. The locations of contact with the engagement plate 54 at the opposite sides are also located at opposite edges of the through hole (i. e. at opposite sides of the engagement plate 54, i. e. on side facing distally and the other side facing proximally).

The engagement for assuming the driving state takes place during an initial relative movement of the movable handle 52 towards the support handle 51. Once the engagement plate 54 and the driving rod 35 are in engagement, upon further actuation of the movable handle 52 in this driving state, the moveable handle 52 increases the inclination of the engagement plate 54. This increase in inclination of the engagement plate 54 pushes the driving rod 35 further towards the limb support 31. During this movement, the inclination of the engagement plate 54 has the advantage to act like a lever arm due to the placement of the engagement plate's pivot axis. This enhances control over the movement of the driving rod 35. The same effect may be achieved by configuring the distance from the end of the movable handle 52 to the pivot axis 53 in relation to the distance from the pivot axis 53 to the contact point with the engagement plate 54.

As described above, the actuation mechanism 50 may further comprise a return biasing means 55. The return biasing means 55 is arranged for biasing the engagement plate 54 towards its initial position. More specifically, the return biasing means 55 is configured to cause the movable handle 52 to return to its initial position upon its release. In other words, the return biasing means 55 causes the engagement plate 54 to tilt backwards so that the movable handle 52 moves (is pushed) back to its initial position.

Further, the engagement plate 54 tilting backwards (i.e., away from the limb support 31) releases the engagement between the engagement plate 54 and the driving rod 35 while the engagement plate 54 returns to its initial position. Accordingly, the movable handle may be actuated several times for driving an interphalangeal implant 10 further towards the limb support 31.

As illustrated in FIGS. 3 and 6, the return biasing means 55 is preferably embodied by an elastic element, such as a spring. Preferably, the elastic element surrounds the driving rod 35 (i.e. the driving rod 35 is insertable into the elastic element). The return biasing means functions to disengage the engagement plate 54 from the driving rod 35 while no external force is applied to the engagement plate 54 or the movable handle 52.

For more reliably preventing the driving rod 35 to move in a proximal direction while the movable handle 52 returns to its initial position, in particular if the driving rod 35 applies pressure during implantation, the actuation mechanism 50 may comprise an engagement biasing means 57 and a retainment plate 56 (cf. FIGS. 3 and 6).

Similar to the engagement plate 54 the retainment plate 56 includes a retainment hole (not illustrated), in particular a through hole), that is dimensioned for an engagement with the driving rod 35. The retainment hole is dimensioned so that the retainment plate 56 and the driving rod 35 are engaged in a retainment state if the retainment plate 56 is tilted relative to the longitudinal axis L of driving rod 35 in relation to a neutral position (i. e. a position, in which the longitudinal axis of the retainment hole is parallel to the longitudinal axis L of the driving rod 35). Accordingly, the driving rod 35 is movable through this retainment hole in a disengaged state whereas is locked to the retainment plate 56 in an engaged state (i. e. while the retainment plate is tilted).

In difference to the engagement plate 54, the retainment plate 56 is not configured to move the driving rod 35 via a handle. Instead, and as already described above, the engagement biasing means 57 keeps the retainment plate in an inclined position away from the limb support. As a result, the driving rod is allowed to move distally and kept from moving proximally.

The engagement biasing means 57 is configured to bias the retainment plate 56 to be tilted relative to the driving rod 35 while no force is applied to the movable handle 52. Thus, the engagement biasing means 57 serves to keep the retainment plate 56 tilted, in particular away from the limb support 31. As a result, the retainment plate 56 and the driving rod 35 are in engagement while no external force is applied that would move the driving rod 35 towards the limb support, i. e. the driving rod 35 is prevented from an unintended translatory movement in the proximal direction of the driving rod 35 (i. e. in its longitudinal direction away from the limb support 31).

Accordingly, the retainment plate 56 and the driving rod 35 are in this retainment state (engaged state) while the engagement plate 54 is in its initial position. In contrast, in the driving state of the engagement plate 54 and the driving rod 35, the retainment plate 56 and the driving rod 35 are able to move relative to each other (i. e. they are not in engagement during a movement of the driving rod 35 in the distal direction).

Consequently, in the actuation mechanism 50, the retainment plate 54 on the one hand and the retainment plate 56 on the other hand have different and mutually complementary purposes that together allow for a coherent movement of the driving rod 35 towards the limb support 31. More specifically, the retainment plate 56 prevents the driving rod 35 from unintentionally moving in a direction away from the limb support 31 (e. g. caused by a release of pressure applied to the interphalangeal implant 10 during implantation), whereas the engagement plate 54 allows for moving the driving rod 35 in a direction towards the limb support 31.

Once the implantation of the interphalangeal implant 10 is finished, the driving rod 35 may be moved proximally back to its initial position for placing an interphalangeal implant 10 by disengaging the retainment plate 56 and the driving rod 35. For example, the retainment plate 56 may have a portion for (manually) tilting the retainment plate 56 against the engagement biasing means 57 to an orientation, in which the longitudinal axis L of the driving rod 35 and the longitudinal axis of the retainment hole are basically parallel (aligned) to each other (i. e. disengaged). This allows a user to move the driving rod 35 along its longitudinal axis L in a proximal direction back to its initial position.

Such configurations of an implantation tool 30 provide for a consistent and particularly controlled movement of an interphalangeal implant 10 towards the limb support 31 and into the implantation site of adjacent interphalangeal bones.

REFERENCE SIGNS

The following is a list of the reference signs used in the detailed description of preferred embodiments and the drawings.
  10 interphalangeal implant
  11 first anchoring section
  12 second anchoring section
  14 central section
  20, 120 implant retainer
  21, 121 jig part
  22, 122 implant aperture
  22a retaining protrusions
  23, 123 holding means
  24, 124 casing retaining structure
  25, 125 implant casing
  26, 126 implant receiving space
  27, 127 jig retaining structure
  28a, 128a snap-fit feature of jig part
  28b, 128b snap-fit feature of implant casing
  30 implantation tool
  31 limb support
  31a supporting groove
  33 male guide member engagement portion
  34 chassis
  35 driving rod
  36 proximal end
  37 distal end
  40 implant guiding means
  41 female guide member
  42 male guide member
  43 female guide member aperture
  44 finger abutment side
  44a contact surface
  44b implantation window
  45 implant holder
  46 pushing portion
  47 driver engagement portion
  50 actuation mechanism
  51 support handle
  52 movable handle
  53 pivot axis
  54 engagement plate
  55 return biasing means
  56 retainment plate
  57 engagement biasing means
  L longitudinal axis

The invention claimed is:
1. An implantation tool for implanting an interphalangeal implant, the implantation tool comprising:
 a limb support for supporting a phalangeal limb;
 a driving rod, wherein the driving rod is movable for moving the interphalangeal implant towards the limb support;
 an actuation mechanism for actuating the driving rod; and
 an implant guiding means for guiding the interphalangeal implant towards the limb support,
 wherein the implant guiding means comprises a female guide member and a male guide member, the female guide member having an aperture facing the limb support, and the male guide member having a pushing portion configured to contact the interphalangeal implant and dimensioned to fit through the aperture of the female guide member,
 wherein the female guide member comprises an implant holder for holding the interphalangeal implant, wherein the implant holder is configured to hold the interphalangeal implant via an interphalangeal implant retainer, and wherein the male guide member comprises a hole that extends parallel to the driving rod, wherein the implant holder is a pin that extends into the hole of the male guide member.

2. The implantation tool according to claim 1, wherein the female guide member of the implant guiding means includes a limb abutment side, the limb abutment side being formed as two contact surfaces protruding from the female guide member, the two contact surfaces arranged on opposite sides of the female guide member aperture.

3. The implantation tool according to claim 1, wherein the male guide member of the implant guiding means further comprises a driver engagement portion for a releasable engagement of the driving rod.

4. The implantation tool according to claim 1, wherein the actuation mechanism is configured to transform a rotatory movement into a translatory movement.

5. The implantation tool according to claim 4, wherein the actuation mechanism comprises a support handle and a movable handle, the movable handle being rotatable about a pivot axis.

6. The implantation tool according to claim 5, wherein
the actuation mechanism further comprises an engagement plate and the driving rod passes through a hole in the engagement plate;
the hole in the engagement plate is dimensioned so that tilting the engagement plate relative to the driving rod starting from an initial position causes the driving rod and the engagement plate to be engaged in a driving state; and
upon actuation of the movable handle, the movable handle first pushes and tilts the engagement plate to assume the driving state so that further movement of the movable handle pushes the driving rod via the engagement plate towards the limb support.

7. The implantation tool according to claim 6, wherein a return biasing means is arranged to bias the engagement plate towards the initial position so that releasing the movable handle causes the engagement plate to return to its initial position.

8. The implantation tool according to claim 6, wherein the actuation mechanism further comprises an engagement biasing means and a retainment plate, the retainment plate including a retainment hole, wherein:
the driving rod is movable through the retainment hole in a disengaged state;
the retainment hole is dimensioned so that the retainment plate and the driving rod are engaged in a retainment state when the retainment plate is tilted relative to the driving rod; and
the engagement biasing means biases the retainment plate to be tilted relative to the driving rod.

9. The implantation tool according to claim 8, wherein
in the initial position of the engagement plate, the retainment plate and the driving rod are in the retainment state; and
in the driving state of the engagement plate and the driving rod, the retainment plate and the driving rod are able to move relative to each other.

10. A method for preparing the implantation tool of claim 1 for implantation of the interphalangeal implant, comprising the steps of:
providing the interphalangeal implant retainer that retains the interphalangeal implant;
bringing a holding means of the interphalangeal implant retainer into engagement with the implant holder of the female guide member; and
actuating the actuation mechanism of the implantation tool to bring the male guide member of the implantation tool into abutment with the interphalangeal implant.

11. The implantation tool according to claim 1, wherein the limb support comprises a longitudinal supporting groove.

12. The implantation tool according to claim 11, wherein the groove comprises a constant cross-section from a first end of the groove to a second end of the groove.

13. The implantation tool according to claim 11, wherein the groove comprises a variable cross-section from a first end of the groove to a second end of the groove.

14. The implantation tool according to claim 13, wherein the groove tapers from a maximum width towards the first end and the second end of the groove toward a width smaller than the maximum width.

* * * * *